United States Patent [19]
Höfert et al.

[11] 4,203,446
[45] May 20, 1980

[54] PRECISION SPRING LANCET

[75] Inventors: Wilhelm A. Höfert, Kollnau; Peter F. Schlüssel, Freiburg; Anton H. Sutor, Freiburg; Georg J. Ullrich, Freiburg, all of Fed. Rep. of Germany

[73] Assignee: Hellige GmbH, Freiburg im Breisgau, Fed. Rep. of Germany

[21] Appl. No.: 828,711

[22] Filed: Aug. 29, 1977

[30] Foreign Application Priority Data

Sep. 24, 1976 [DE] Fed. Rep. of Germany ....... 2642896

[51] Int. Cl.² .................................... A61B 17/34
[52] U.S. Cl. ........................... 128/329 R; 81/52.35; 173/119; 173/114; 173/139; 227/132; 72/456; 72/465
[58] Field of Search .................. 128/329 R, 305, 314, 128/316, 173 H, 330; 72/456, 465; 81/52.35; 30/277; 173/119, 114, 139; 227/132, 133

[56] References Cited

U.S. PATENT DOCUMENTS

| | | | |
|---|---|---|---|
| 3,208,452 | 9/1965 | Stern | 128/329 X |
| 3,788,404 | 1/1974 | Kondelka et al. | 173/139 |

FOREIGN PATENT DOCUMENTS

119309 10/1959 U.S.S.R. .................................. 128/329

OTHER PUBLICATIONS

Sutor et al., "Automated Technique for Recording Time, Intensity and Pattern for Bleeding", American Journal of Clinical Pathology, vol. 55, 1971, pp. 541-550.
Lampel et al., Waffenlexikon fuer Jaeger und Schuetzen, (Lexicon of Weapons for Hunters and Sharpshooters), published by F. C. Mayer-Verlag in Muenchen-Solln, 1963, 5th Ed., p. 83.

*Primary Examiner*—Henry J. Recla
*Attorney, Agent, or Firm*—Norman E. Brunell; W. R. Thiel

[57] ABSTRACT

A spring lancet holder for creating accurate standardized, reproducible puncture wounds in the skin for medical diagnostic purposes is disclosed in which accuracy and reproducibility is improved by minimizing the recoil transmitted to the lancet holder by actuation of the drive mechanism which pushes the lancet into the skin. In a preferred embodiment, a mass is shown which is caused to move in opposition to the motion of the lancet caused by a striker spring which is mounted between the lancet and the mass.

8 Claims, 1 Drawing Figure

U.S. Patent    May 20, 1980    4,203,446
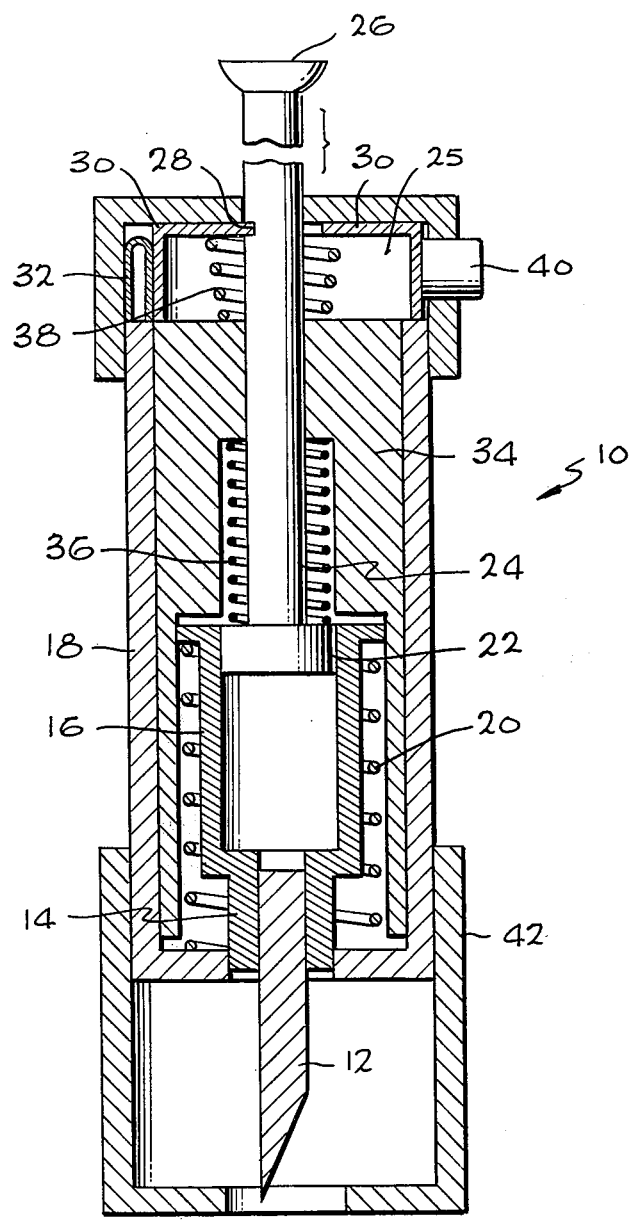

PRECISION SPRING LANCET

BACKGROUND OF THE INVENTION

1. Field of the Invention

This invention relates to apparatus for inflicting standard puncture wounds in the skin for medical diagnosis. Many medical procedures such as those for the diagnosis of disturbances of hemostasis and blood coagulation and the like require the artificial creation of a small standard wound of a known size with great accuracy in order to obtain reproducible results. A common procedure of this sort is the determination of bleeding time. A new procedure was recently developed at the Mayo Clinic in Rochester, Minnesota, to automatically determine the pattern of bleeding. This invention particularly relates to lancet holders, also called "spring lancets" of the type used to create artificial, standard wounds in the earlobe or fingertip or other skin surface of a highly accurate and consistent size.

2. Description of the Prior Art

The conventional lancet holder provides a lancet or blade that is guided in a tube which is placed upon the spot where the wound is to be created. Upon actuation of a trigger mechanism, the lancet is hurled from the tube and thus inflicts a wound whose depth and/or size may be only very coarsely controlled. In order to prevent infection, disposable lancets are sometimes utilized. One difficulty with such devices with regard to the reproducibility of the size of the wound is that the lancet is removed from the skin when the lancet holder is drawn away from the surface of the skin by the medical technician. The skill of the technician therefore greatly affects the accuracy of the size of the standard wound created by the lancet.

An improvement on the conventional lancet holder is known in which the lancet is automatically drawn out of the wound after puncture. This device is described in the article by A. H. Sutor, E. J. Bowie, J. H. Thompson, Jr., P. Didisheim, B. F. Mertens and C. A. Owen, Jr., entitled "Automated Technique for Recording Time, Intensity and Pattern of Bleeding", in the *American Journal of Clinical Pathology*, Vol. 55, 1971, pp. 541–550. It has been found, however, that some practice with the device was required in order to obtain reproducible results. This requirement for practice may be traceable to inaccuracies due to the recoil and rebound transmitted to the lancet holder on triggering of the spring lancet. With this known device the skill of the technician is therefore still a vital factor in creating wounds of a predetermined standardized size.

These conditions are analagous to a shot fired from a pistol, which requires a great deal of practice before the person holding the pistol learns to compensate accurately for recoil. Air power pistols are known, however, which have mass and motion compensation to minimize recoil. See, for example, the book *Waffenlexikon fuer Jaeqer und Schuetzen* (Lexicon of Weapons for Hunters and Sharpshooters) by W. Lampel and R. Mahrholdt, published by F. C. Mayer-Verlag in Muenchen-Solln, 1963, 5th ed., page 83. In weapons of this sort, impact rebound and recoil are compensated by forces of opposition provided by cylinders of equal weight.

SUMMARY OF THE INVENTION

It is a primary object of the instant invention to provide a lancet holder for the production of standardized wounds of maximum accuracy and reproducibility without the requirement of operation by a skilled practitioner. This object is achieved and the disadvantages of the prior art are avoided by a lancet holder which makes possible recoilless triggering of the lancet. Recoilless triggering of the lancet improves the accuracy and reproducibility of standardized wounds because when the lancet is activated and pierces the skin, the lancet holder remains to a great extent unmoved. The wound size is therefore not disturbed by any unsteadiness in the positioning, holding or removal from the skin of the lancet holder. The goal is therefore to absorb the recoil of the lancet as it shoots forward into the skin without transmitting the forces of acceleration to the lancet holder. Recoil can be prevented by pneumatic or hydraulic devices analagous to recoilless firearms, by mechanical devices such as compensatory weights, cushioning springs and return springs and by electronic means cooperating with acceleration sensors.

Recoilless triggering of the lancet may also be accomplished with pressurized gas, such as carbon dioxide ($CO_2$). In such a device a predetermined volume of $CO_2$ stored in a cartridge would be delivered, by the operation of a trigger valve, into a pressure chamber including a piston to which the lancet is affixed. When the piston has reached its full forward position it would actuate a valve to relieve pressure from the chamber. A restoring spring would then withdraw the lancet from the skin.

In a preferred embodiment of the instant invention, the lancet holder is a mechanical, spring-operated lancet holder called a "spring lancet". The lancet is held in a collar and is driven into the surface of the skin with a precisely adjusted stroke from a spring actuated striker. The lancet is then automatically withdrawn from the skin by means of a return spring. In order to prevent recoil of the lancet holder, actuation of the lancet causes a compensatory mass to be moved in an opposite direction.

BRIEF DESCRIPTION OF THE DRAWING

The FIGURE is a side view in cross-section of a spring lancet holder providing for recoilless actuation of the lancet according to the instant invention.

DETAILED DESCRIPTION OF A PREFERRED EMBODIMENT

Recoilless spring lancet holder 10 is shown in the FIGURE including lancet 12 which may conveniently be a knife blade of conventional construction. Blade 12 is mounted within collar 14 which is formed at one end of blade guide 16 which is mounted for motion within housing 18. As shown in the FIGURE, blade guide 16 may be moved vertically downward so that collar 14 extends through the opening at the lower end of housing 18. Retarding this downward motion is restoring spring 20. At the end of blade guide 16 opposite to the end at which collar 14 is mounted, blade guide 16 is formed as a hollow cylinder. Mounted therein for motion is striker plate 22 fastened to striker shaft 24 which continues through an opening at the other end of housing 18. The uppermost end of shaft 24 includes handle 26. Striker shaft 24 includes groove 28 in which locking plate 30 is urged by spring 32 when recoilless spring lancet 10 is in the armed position ready for actuation.

Locking plate 30 also serves to prevent upward motion of mass 34 contained within housing 18 and coaxial with shaft 24. Striker spring 36 is positioned in the interior space shown between mass 34 and striker shaft 24. Striker spring 36 is affixed at the uppermost end to mass 34 and at the lowermost end to striker plate 22.

In the embodiment shown in the FIGURE, recoilless spring lancet holder 10 is armed and ready for actuation so that striker spring 36 is compressed. Restoring spring 20 is not compressed and impact spring 38 mounted between locking plate 30 and the upper end of mass 34 is also not compressed.

Trigger button 40 protrudes through an opening in housing 18 and is connected to locking plate 30. When button 40 is activated, locking plate 30 will move out of contact with groove 28 releasing striker plate 22 which is urged downward by spring 36. Striker plate 22 continues downward within blade guide 16 until it strikes the upper end of collar 14. At this impact, collar 14 and therefore lancet 12 are both urged downwardly so that lancet 12 pierces the skin. After this force is removed because spring 36 has reached the end of its travel, restoring spring 20 serves to move lancet 12 vertically upward to remove it from the standard wound.

It is extremely important, however, to note that striker spring 36 which urges striker shaft 24 vertically downward to cause piercing of the skin is mounted between striker plate 22 and compensating mass 34. Therefore, when button 40 is pushed to activate the lancet, mass 34 is urged vertically upward against spring 38 as mass 34 moves into area 25 within housing 18. This compensatory movement of mass 34 serves to minimize transmission to housing 18 of the recoil and impact rebound caused by the triggering. It is this feature which improves the lancet holder of the instant invention.

The depth of incision may be controlled by positioning of jacket sleeve 42 mounted at the lower end of housing 18. Sleeve 42 has a hole in the bottom thereof through which lancet 12 is allowed to pass. Sleeve 42 may be positioned vertically on housing 18 to control the maximum exposure of lancet 12. This, of course, controls the depth of the puncture. The width of the puncture is controlled by the size and shape of the sharpened lower edge of lancet 12.

Although the improved recoilless spring lancet described relies upon the compensatory motion of mass 34 to reduce recoil transmitted to housing 18, it is possible as described hereinabove to provide many other types of compensatory or recoil-preventing forces without departing from the spirit or scope of the invention which is defined by the following claims.

We claim:

1. An improved lancet holder for the creation of standard puncture wounds in the skin for diagnostic purposes of the type having a housing, a lancet mounted for motion in the housing, means for urging the lancet into contact with the skin, a trigger for activating the urging means, and means for withdrawing the lancet from the skin after contact therewith, wherein the improvement comprises:

means for preventing recoil of the lancet holder in response to the activation of the urging means wherein the recoil preventing means includes a mass mounted for motion in the housing in opposition to the motion of the lancet upon activation by the trigger.

2. The improved lancet holder claimed in claim 1 wherein the mass moves away from the skin when the lancet is urged into contact therewith.

3. The improved lancet holder claimed in claim 1 wherein an impact spring is provided between the mass and the housing to resist motion therebetween.

4. The improved lancet holder claimed in claim 1 wherein the means for urging the lancet includes a striker spring mounted at one end to the mass.

5. The improved lancet holder claimed in claim 4 wherein a collar is provided for mounting the lancet and a striker plate is provided at a second end of the striker spring for contact with the collar.

6. The improved lancet holder claimed in claim 5 wherein the trigger includes means for releasably maintaining the striker spring in compression.

7. The improved lancet holder claimed in claim 6 wherein the striker plate is maintained out of contact with the collar until the trigger is activated.

8. The improved lancet holder claimed in claim 5 wherein the means for withdrawing the lancet includes a restoring spring mounted between the collar and the housing to resist motion of the lancet toward the spring.

* * * * *